(12) United States Patent
Zhou et al.

(10) Patent No.: US 10,502,432 B2
(45) Date of Patent: Dec. 10, 2019

(54) KITCHEN APPLIANCE COMPRISING DRAWER

(71) Applicants: GUANGDONG MIDEA KITCHEN APPLIANCES MANUFACTURING CO., LTD., Foshan (CN); MIDEA GROUP CO., LTD., Foshan (CN)

(72) Inventors: Jianyi Zhou, Foshan (CN); Yongzhong Zhang, Foshan (CN); Jian Long, Foshan (CN)

(73) Assignees: GUANGDONG MIDEA KITCHEN APPLIANCES MANUFACTURING CO., LTD., Foshan (CN); MIDEA GROUP CO. LTD., Foshan (CN)

( * ) Notice: Subject to any disclaimer, the term of this patent is extended or adjusted under 35 U.S.C. 154(b) by 0 days.

(21) Appl. No.: 16/047,993

(22) Filed: Jul. 27, 2018

(65) Prior Publication Data
US 2018/0372328 A1    Dec. 27, 2018

Related U.S. Application Data

(63) Continuation of application No. PCT/CN2016/077793, filed on Mar. 30, 2016.

(30) Foreign Application Priority Data

Feb. 1, 2016    (CN) .......................... 2016 1 0070836

(51) Int. Cl.
*F24C 15/02* (2006.01)
*F24C 15/16* (2006.01)

(52) U.S. Cl.
CPC .......... *F24C 15/022* (2013.01); *F24C 15/162* (2013.01)

(58) Field of Classification Search
CPC .................. F24C 15/022; F24C 15/164; E05B 63/0052; E05B 65/0014; E05C 3/04; A47B 88/50
(Continued)

(56) References Cited

U.S. PATENT DOCUMENTS 3,797,871 A * 3/1974 Morishita ............. E05B 65/102
16/333
5,114,194 A * 5/1992 Toifl .................... E05B 65/0014
292/106

(Continued)

FOREIGN PATENT DOCUMENTS

| CN | 202066291 U | 12/2011 | |
| CN | 102390534 A | 3/2012 | |
| EP | 2851492 A1 * | 3/2015 | ......... E05B 65/0014 |

*Primary Examiner* — Daniel J Rohrhoff
(74) *Attorney, Agent, or Firm* — Morgan, Lewis & Bockius LLP

(57) ABSTRACT

The present disclosure provides a kitchen appliance with a drawer. The kitchen appliance has a body, a drawer and a position-limiting lock assembly. The drawer is located in an accommodation cavity of the body. The position-limiting lock assembly has a lock and is mounted on the body and above the accommodation cavity. One end of the lock is rotatably connected to the body, and the other end of the lock protrudes from the front opening of the body. When the other end of the lock rotates to a position in front of the drawer cover, the drawer is restrained from being pulled out of the accommodation cavity; when the other end of the lock rotates away from the position in front of the drawer cover, the drawer can be pulled out of the accommodation cavity, thereby preventing the drawer from being accidentally opened in movement settings.

6 Claims, 9 Drawing Sheets

(58) Field of Classification Search
USPC .................................................. 292/94, 194
See application file for complete search history.

(56) References Cited

U.S. PATENT DOCUMENTS

| | | | | |
|---|---|---|---|---|
| 6,930,284 | B2* | 8/2005 | Kang .................... | F24C 15/022 |
| | | | | 126/197 |
| 9,322,192 | B2* | 4/2016 | Burd .................. | B64D 11/0007 |
| 2007/0262590 | A1* | 11/2007 | Courter ............... | E05B 17/0029 |
| | | | | 292/201 |
| 2013/0020814 | A1* | 1/2013 | McConnell ........... | E05B 53/001 |
| | | | | 292/194 |
| 2016/0159570 | A1* | 6/2016 | Reeb ..................... | B65F 1/1615 |
| | | | | 220/324 |

* cited by examiner

KITCHEN APPLIANCE COMPRISING DRAWER

PRIORITY CLAIM AND RELATED APPLICATION

This application is a continuation of PCT Patent Application No. PCT/CN2016/077793, entitled "KITCHEN APPLIANCE COMPRISING DRAWER" filed on Mar. 30, 2016, which claims priority to Chinese Patent Application No. 201610070836.8, entitled "KITCHEN APPLIANCE COMPRISING DRAWER" filed on Feb. 1, 2016, all of which are hereby incorporated by reference in their entirety.

TECHNICAL FIELD

The present disclosure relates to the field of kitchen utensils, and more specifically, relates to a kitchen appliance with a drawer.

BACKGROUND

When the existing household appliances comprising drawers, such as drawer type microwave ovens, drawer type ovens, drawer type sterilizer cabinets, drawer type dishwashers, etc., are installed in movement settings of limos, trains and the like, the drawers are opened due to the action of inertia or due to the geographical condition, uneven road condition and the like, resulting in the contents therein being thrown out to cause hidden danger. Besides, the drawers are easily opened by children to pinch hands or scald them or cause other risks.

SUMMARY

The present disclosure aims to solve at least one of the technical problems in the prior art.

To this end, the objective of the present disclosure is to provide a kitchen appliance with a drawer that can be locked.

To achieve the above objective, the embodiments of the present disclosure provide a kitchen appliance with a drawer, comprising: a body having an accommodation cavity of which a front end is provided with an opening; a drawer located in the accommodation cavity, wherein a drawer cover is fixedly attached to a front end of the drawer, and the drawer cover can drive the drawer to move relative to the body, so as to draw the drawer out of or push the drawer into the accommodation cavity; and a position-limiting lock assembly mounted on the body and above the accommodation cavity, wherein the position-limiting lock assembly has a lock, one end of the lock being rotatably connected to the body and the other end of the lock protruding from a front opening of the body, when the other end of the lock rotates to a position in front of the drawer cover, the drawer is restrained from being pulled out of the accommodation cavity, and when the other end of the lock rotates away from the position in front of the drawer cover, the drawer can be pulled out of the accommodation cavity.

In the kitchen appliance with a drawer according to the above embodiment of the present disclosure, e.g. a microwave oven with a drawer, an oven with a drawer, a sterilizer cabinet with a drawer and a dishwasher with a drawer, one end of a lock is rotatably connected to the body, and the other end of the lock protrudes from the front opening of the body. The other end of the lock can rotate to a position in front of the drawer cover to lock the drawer cover such that the drawer cover cannot be pulled out forward and the drawer cannot be pulled out of the accommodation cavity. In this way, when the microwave oven with a drawer is applied to a mobile environment such as a train, the drawer will not be opened due to inertia or road unevenness or other external factors, thereby preventing the contents inside the drawer from being thrown out, preventing children from opening the drawer and exposing themselves to danger such as pinching or scald, and enhancing the use safety of the microwave oven with a drawer. When the drawer needs to be opened, the other end of the lock is rotated away from a position in front of the drawer cover to unlock the drawer cover, and the drawer cover is pulled to draw the drawer out of the accommodation cavity. When the drawer cover and the drawer need to be locked again, the drawer is pushed into the accommodation cavity, and the other end of the lock is rotated from a position separated from the front of the drawer cover to the front of the drawer cover.

In addition, the kitchen appliance with a drawer according to the above embodiment of the present disclosure also has the following additional technical features:

according to one embodiment of the present disclosure, the position-limiting lock assembly is located close to a side wall of the body, one end of the lock is rotatably connected to the body through a rotating shaft, and the rotating shaft is arranged in the vertical direction such that the lock can rotate within a horizontal plane from the front of the drawer cover to a side of the drawer cover.

In the above embodiment, when the lock rotates within a horizontal plane and the other end of the lock rotates to the front of the drawer cover, the drawer cover is locked to restrict the drawer from being pulled out of the accommodation cavity; and when the drawer needs to be opened, the other end of the lock is rotated to the side of the drawer cover to unlock the drawer cover, and the drawer cover is pulled to draw the drawer out.

According to one embodiment of the present disclosure, the lock is L-shaped and comprises a first connecting portion and an extending portion formed by bending extension of the first connecting portion, the first connecting portion is rotatably connected to the body through the rotating shaft, and the extending portion can rotate to the front and the side of the drawer cover.

In the above embodiment, the extending portion protrudes from the front opening of the accommodation cavity and the side wall of the body, and the extending portion is rotated such that an extending portion is located in front of the drawer cover to lock the drawer cover; and the extending portion is rotated from the front of the drawer cover to the side of the drawer cover to unlock the drawer cover.

Preferably, a protective sleeve is sleeved on the extending portion to prevent the extending portion from scratching a user during rotating, and also to prevent the extending portion from scratching the drawer cover and the body.

According to one embodiment of the present disclosure, the front end of the body is provided with a control panel, the control panel is located above the drawer cover, and the first connecting portion is located between the drawer cover and the control panel and rotatably connected to a bottom surface of the control panel through the rotating shaft.

In the above embodiment, a first connecting portion is located between the lower end face of a control panel and the upper end face of the drawer cover and rotatably connected to a bottom surface of the control panel through a rotating shaft such that the extending portion can rotate relative to the drawer cover to lock and unlock the drawer cover, and the first connecting portion is located between the control panel and the drawer cover such that the installation of the lock does not affect the structure and whole attractiveness of the microwave oven with a drawer.

According to one embodiment of the present disclosure, the position-limiting lock assembly further comprises a fixed base, the fixed base comprises a fixed portion and a second connecting portion connected to the fixed portion, the fixed portion is fixed on a rear side of the control panel, the second connecting portion is located between the control panel and the drawer cover, and the first connecting portion is rotatably connected to the second connecting portion through the rotating shaft.

In the above embodiment, a fixed base is fixed on a rear side of the control panel, the lock is connected to the fixed base, and then the control panel is installed on the body to install and fix the position-limiting lock assembly on the body simply and easily without affecting the overall structure of the microwave oven with a drawer; and the first connecting portion is rotatably connected to a second connecting portion through the rotating shaft such that the lock can rotate relative to the fixed base and the extending portion can rotate to the front and the side of the drawer cover. Preferably, the fixed base is L-shaped, and the plane where the first connecting portion is located is parallel to the plane where the second connecting portion is located.

As for the fixing of the fixed base on the control panel, preferably, the fixed portion is provided with a screw hole, screw columns are arranged on a rear side of the control panel, and the fixed base is fixed on the control panel through a screw.

According to an embodiment of the present disclosure, the first connecting portion is connected to the second connecting portion through a rivet, and an elastic gasket is arranged between the rivet and the first connecting portion, thereby enhancing the mobility of the first connecting portion relative to the second connecting portion, and relieving the friction between the first connecting portion and the second connecting portion.

According to one embodiment of the present disclosure, the surface of the first connecting portion opposite to the second connecting portion protrudes to form a protrusion, and the second connecting portion is provided with a first limiting hole and a second limiting hole matched with the protrusion; when the extending portion rotates to the front of the drawer cover, the protrusion is inserted into the first limiting hole; and when the extending portion rotates to the side of the drawer cover, the protrusion is inserted into the second limiting hole.

In the above embodiment, when the extending portion rotates to the front and the side of the drawer cover, a protrusion is inserted into a first limiting hole and a second limiting hole respectively to position the lock and prevent the user from excessively rotating the lock or failing to rotate the lock in place, so that the locking effect of the lock on the drawer cover is best, and the user can freely draw the drawer out. Of course, the first connecting portion may also be provided with a limiting hole, the second protruding portion is provided with a first protrusion and a second protrusion on the end face opposite to the first connecting portion, and when the drawer cover is unlocked or locked, the first protrusion and the second protrusion are inserted into the limiting hole respectively.

Preferably, the protrusion and the extending portion are located on two sides of the rivet on the first connecting portion, that is, the protrusion is located at the free end of the first connecting portion. Since the free end has good elastic deformation capability, when the protrusion is arranged at the free end, the first connecting portion can be positioned, and the rotating capability of the lock relative to the fixed base is not reduced.

According to one embodiment of the present disclosure, both the first limiting hole and the second limiting hole are elliptical, and major axes of the two ellipses are perpendicular to each other.

In the above embodiment, preferably, the long axes of ellipses are located in the radial direction of rotation of the first connecting portion, so as to enhance the positioning capability of the first limiting hole and the second limiting hole to the protrusion. The straight lines where the long axes of the two ellipses are located are perpendicular to each other such that when the drawer cover enters the unlocked state from the locked state, the first connecting portion is rotated 90° conveniently; when the drawer cover is in the locked state, the extending portion is located in front of the drawer cover to achieve a best locking effect; and when the drawer cover is in the unlocked state, the extending portion is completely located on the side of the drawer cover and does not interfere with the draw-out operation on the drawer cover to ensure that the drawer cover is freely drawn out and pushed in.

According to one embodiment of the present disclosure, the second connecting portion forms a first limit stop and a second limit stop both facing the first connecting portion, and the first connecting portion is configured to rotate within a limit space formed by the first limit stop and the second limit stop; when the extending portion rotates to the front of the drawer cover, one side wall of the first connecting portion abuts against the first limit stop; and when the extending portion rotates to the side of the drawer cover, the other side wall of the first connecting portion abuts against the second limit stop.

In the above embodiment, the extending portion rotates between a first limit stop and a second limit stop. When the drawer cover is locked, one side wall of the first connecting portion abuts against the first limit stop, and when the drawer cover is unlocked, the other side wall of the first connecting portion abuts against the second limit stop, thereby limiting the angle range of rotation of the lock. When the user uses it, the extending portion is rotated to a position where the side wall of the first connecting portion abuts against the first limit stop or the second limit stop, such that the drawer cover is completely locked or unlocked. Preferably, the second connecting portion is provided with the first limiting hole, the second limiting hole, the first limit stop and the second limit stop at the same time, so that when the protrusion is separated from the first limiting hole or the second limiting hole due to overexertion of the user rotating the lock, the first limit stop and the second limit stop can continue to play a role in limiting and positioning to enhance the use reliability and stability of the position-limiting lock assembly.

Preferably, the microwave oven with a drawer is provided with two position-limiting lock assemblies, the two position-limiting lock assemblies are respectively located at the left and right ends of the control panel, the right lock is rotated right to the right side of the drawer cover, and the left lock is rotated left to the left side of the drawer cover, thus unlocking the drawer cover; and the right lock is rotated left to the front of the drawer cover, and the left lock is rotated right to the front of the drawer cover, thus locking the drawer cover.

According to one embodiment of the present disclosure, the position-limiting lock assembly is located on the front end face of the body, one end of the lock is rotatably connected to the body through the rotating shaft, and the rotating shaft is arranged in the horizontal direction, so that the lock rotates within a vertical plane and can rotate to the front of the drawer cover and above the drawer cover.

In the above embodiment, the position-limiting lock assembly is located on the front end face of the body and above the accommodation cavity, one end of the lock is rotatably connected to the body through the rotating shaft, the other end protrudes from the front opening of the accommodation cavity, and the lock rotates within the vertical plane; when the lock rotates down, the other end of the lock is located in front of the drawer cover to lock the drawer cover; and when the lock rotates up, the other end of the lock is located above the drawer cover to unlock the drawer cover.

Preferably, the microwave oven with a drawer can be installed in a cabinet.

Additional aspects and advantages of the present disclosure will become apparent in the following description, or may be learned by practice of the present disclosure.

BRIEF DESCRIPTION OF THE DRAWINGS

The above and/or additional aspects and advantages of the present disclosure will become apparent and be easily understood from the following description of embodiments in conjunction with the accompanying drawings, in which.

Figure 1:
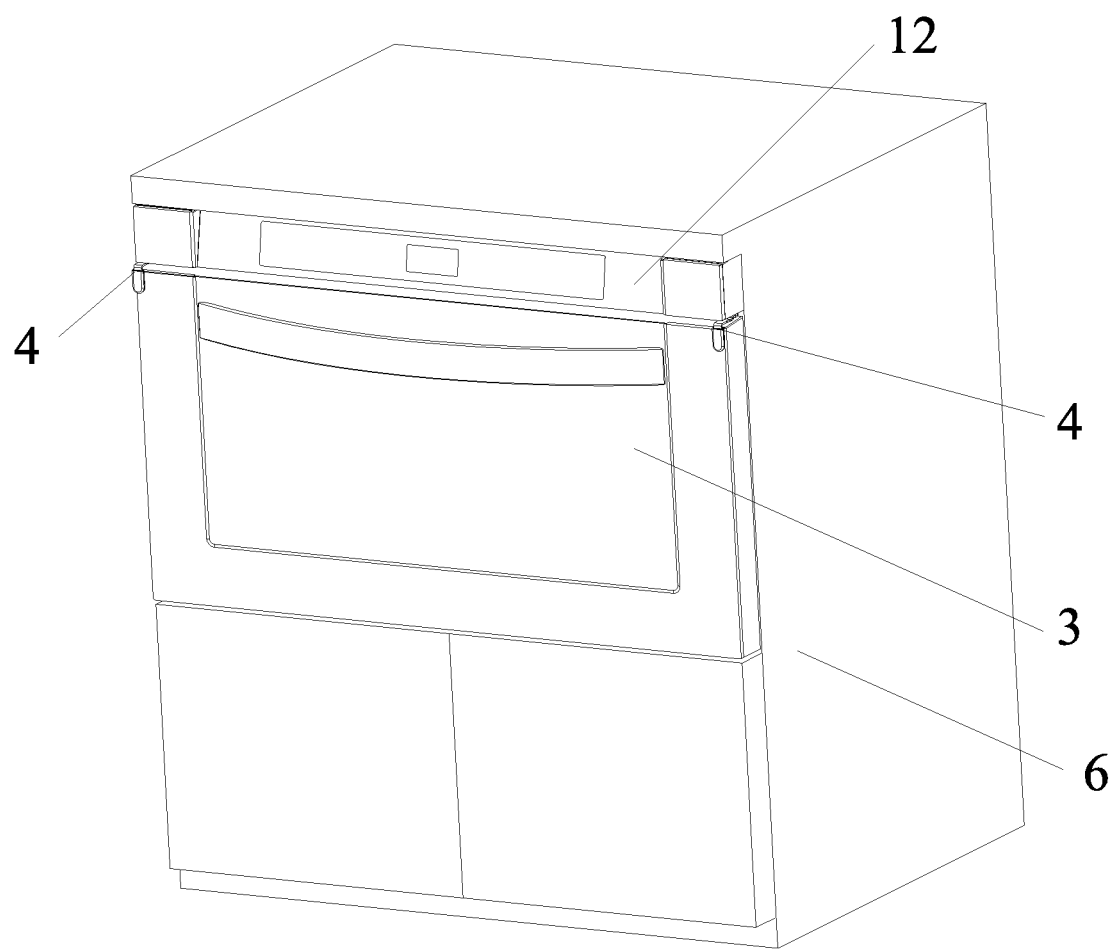
FIG. 1 is a three-dimensional structure diagram indicating that a microwave oven with a drawer is assembled with a cabinet according to an embodiment of the present disclosure.

The correspondence between the reference signs and the component names in FIG. 1 to FIG. 13 is:
100—microwave oven with drawer;
1—body;
11—accommodation cavity;
12—control panel;
121—screw column;
2—drawer;
3—drawer cover;
4—position-limiting lock assembly;
41—lock;
411—first connecting portion;
4111—protrusion;
412—extending portion;
42—fixed base;
421—fixed portion;
4211—screw hole;
422—second connecting portion;
4221—first limiting hole;
4222—second limiting hole;
4223—first limit stop;
4224—second limit stop;
43—rivet;
44—elastic gasket;
45—protective sleeve;
5—screw; and
6—cabinet.

DETAILED DESCRIPTION

In order to understand the above objectives, features and advantages of the present disclosure more clearly, the present disclosure will be further described in detail below in conjunction with the accompanying drawings and specific embodiments. It should be noted that the embodiments of the present application and features in the embodiments can be combined with each other without conflicts.

In the following description, numerous specific details are set forth in order to fully understand the present disclosure. However, the present disclosure can also be implemented in other ways than those described herein. Therefore, the scope of the present disclosure is not limited to the specific embodiments disclosed below.

A kitchen appliance with a drawer according to some embodiments of the present disclosure will be described below with reference to the accompanying drawings and a microwave oven with a drawer.

As shown in FIG. 1 to FIG. 6, a kitchen appliance with a drawer according to some embodiments of the present disclosure includes a body 1, the drawer 2 and a position-limiting lock assembly 4.

The body 1 includes an accommodation cavity 11 of which the front end is provided with an opening;

The drawer 2 is located in the accommodation cavity 11, a drawer cover 3 is fixedly connected to a front end of the drawer 2, and the drawer cover 3 can drive the drawer 2 to move relative to the body 1, so as to draw the drawer 2 out of or push the drawer 2 into the accommodation cavity 11;

The position-limiting lock assembly 4 is mounted on the body 1 and above the accommodation cavity 11 and includes a lock 41, one end of the lock 41 is rotatably connected to the body 1, the other end of the lock 41 protrudes from the front opening of the body 1, the other end of the lock 41 can rotate to a position in front of the drawer cover 3 such that the drawer 2 is restrained from being pulled out of the accommodation cavity 11, and the other end of the lock 41 can be rotated away from a position in front of the drawer cover such that the drawer 2 is able to be pulled out of the accommodation cavity 11.

In the kitchen appliance with a drawer according to the above embodiment of the present disclosure, e.g. a microwave oven 100 with a drawer, an oven with a drawer, a sterilizer cabinet with a drawer and a dishwasher with a drawer, one end of the lock 41 is rotatably connected to the body 1, and the other end of the lock 41 protrudes from the front opening of the body 1. The other end of the lock 41 can rotate to a position in front of the drawer cover 3 to lock the drawer cover 3 such that the drawer cover 3 cannot be pulled out forward and the drawer 2 cannot be pulled out of the accommodation cavity 11. In this way, when the microwave oven 100 with a drawer is applied to a mobile environment such as a train, the drawer 2 will not be opened due to inertia or road unevenness or other external factors, thereby preventing the contents inside the drawer 2 from being thrown out, preventing children from opening the drawer 2 and exposing themselves to danger such as pinching or scald, and enhancing the use safety of the microwave oven 100 with a drawer. When the drawer 2 needs to be opened, the other end of the lock 41 is rotated away from a position in front of the drawer cover 3 to unlock the drawer cover 3, and the drawer cover 3 is pulled to draw the drawer 2 out of the accommodation cavity 11. When the drawer cover 3 and the drawer 2 need to be locked again, the drawer 2 is pushed into the accommodation cavity 11, and the other end of the lock 41 is rotated from a position separated from the front of the drawer cover 3 to the front of the drawer cover 3.

In the first embodiment of the present disclosure, as shown in FIGS. 1 to 6, the position-limiting lock assembly 4 is located close to a side wall of the body 1, one end of the lock 41 is rotatably connected to the body 1 through a rotating shaft, and the rotating shaft is arranged in the vertical direction such that the lock 41 rotates within a horizontal plane and can rotate to the front of the drawer cover 3 and the side of the drawer cover 3.

In the above embodiment, when the lock 41 rotates in the horizontal plane and the other end of the lock 41 rotates to the front of the drawer cover 3, the drawer cover 3 is locked to restrict the drawer 2 from being pulled out of the accommodation cavity 11. When the drawer 2 needs to be opened, the other end of the lock 41 is rotated to the side of the drawer cover 3 to unlock the drawer cover 3, and the drawer cover 3 is pulled to draw the drawer 2 out.

Figure 7:
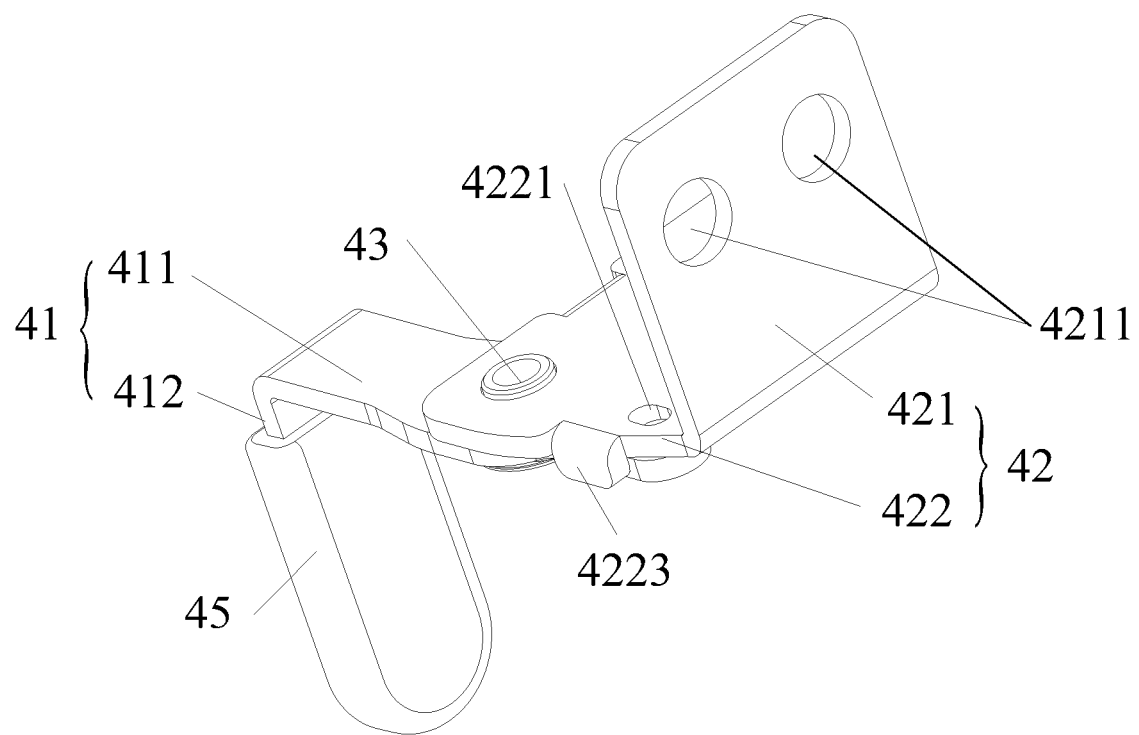
FIG. 7 is a three-dimensional structure diagram of a position-limiting lock assembly according to an embodiment of the present disclosure.
Figure 8:
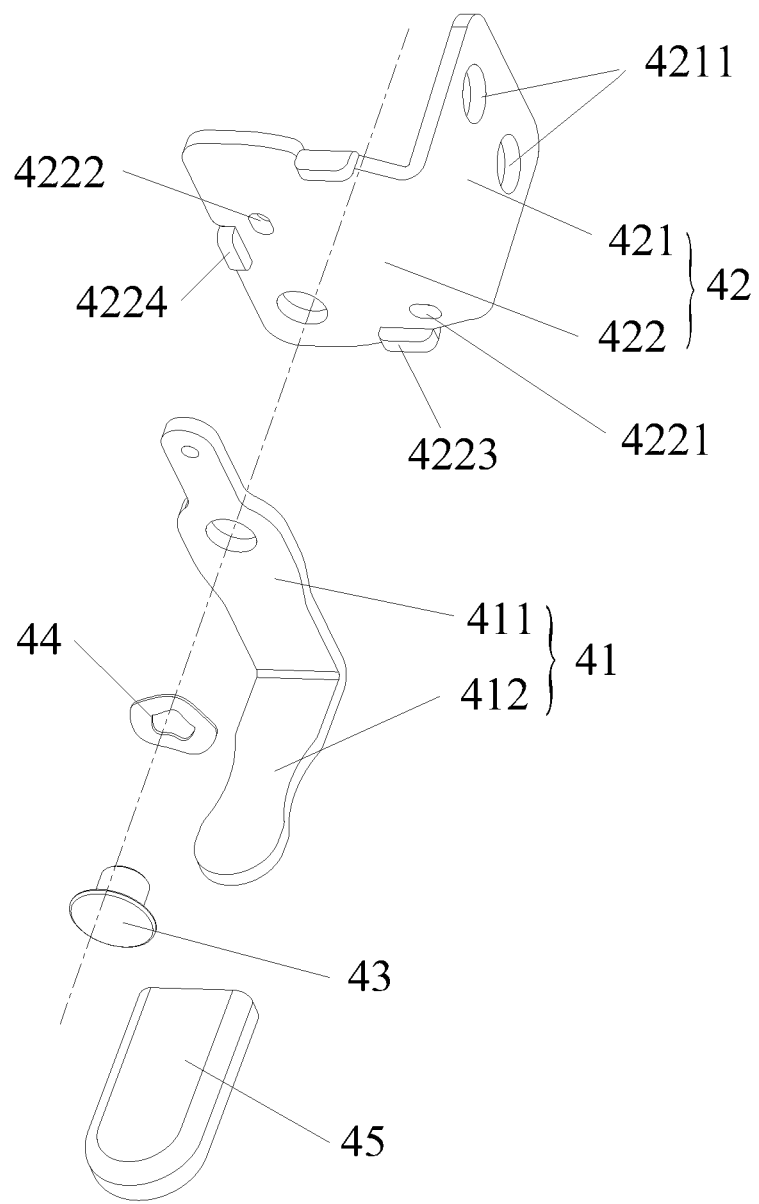
FIG. 8 is an exploded structure diagram of the position-limiting lock assembly shown in FIG. 7.

In an embodiment of the present disclosure, as shown in FIG. 7 and FIG. 8, the lock 41 is L-shaped and includes a first connecting portion 411 and an extending portion 412 formed by bending extension of the first connecting portion 411, the first connecting portion 411 is rotatably connected to the body 1 through the rotating shaft, and the extending portion 412 can rotate to the front and the side of the drawer cover 3.

In the above embodiment, the extending portion 412 protrudes from the front opening of the accommodation cavity 11 and the side wall of the body 1, and the extending portion 412 is rotated such that the extending portion 412 is located in front of the drawer cover 3 to lock the drawer cover 3; and the extending portion 412 is rotated from the front of the drawer cover 3 to the side of the drawer cover 3 to unlock the drawer cover 3.

Preferably, as shown in FIG. 7 and FIG. 8, a protective sleeve 45 is sleeved on the extending portion 412 to prevent the extending portion 412 from scratching a user during rotating, and also to prevent the extending portion 412 from scratching the drawer cover 3 and the body 1.

In an embodiment of the present disclosure, as shown in FIG. 1 to FIG. 6, the front end of the body 1 is provided with a control panel 12, and the control panel 12 is located above the drawer cover 3. The first connecting portion 411 is located between the drawer cover 3 and the control panel 12 and rotatably connected to a bottom surface of the control panel 12 through the rotating shaft.

In the above embodiment, the first connecting portion 411 is located between the lower end face of the control panel 12 and the upper end face of the drawer cover 3 and rotatably connected to a bottom surface of the control panel 12 through the rotating shaft such that the extending portion 412 can rotate relative to the drawer cover 3 to lock and unlock the drawer cover 3, and the first connecting portion 411 is located between the control panel 12 and the drawer cover 3 such that the installation of the lock 41 does not affect the structure and whole attractiveness of the microwave oven 100 with a drawer.

Figure 9:
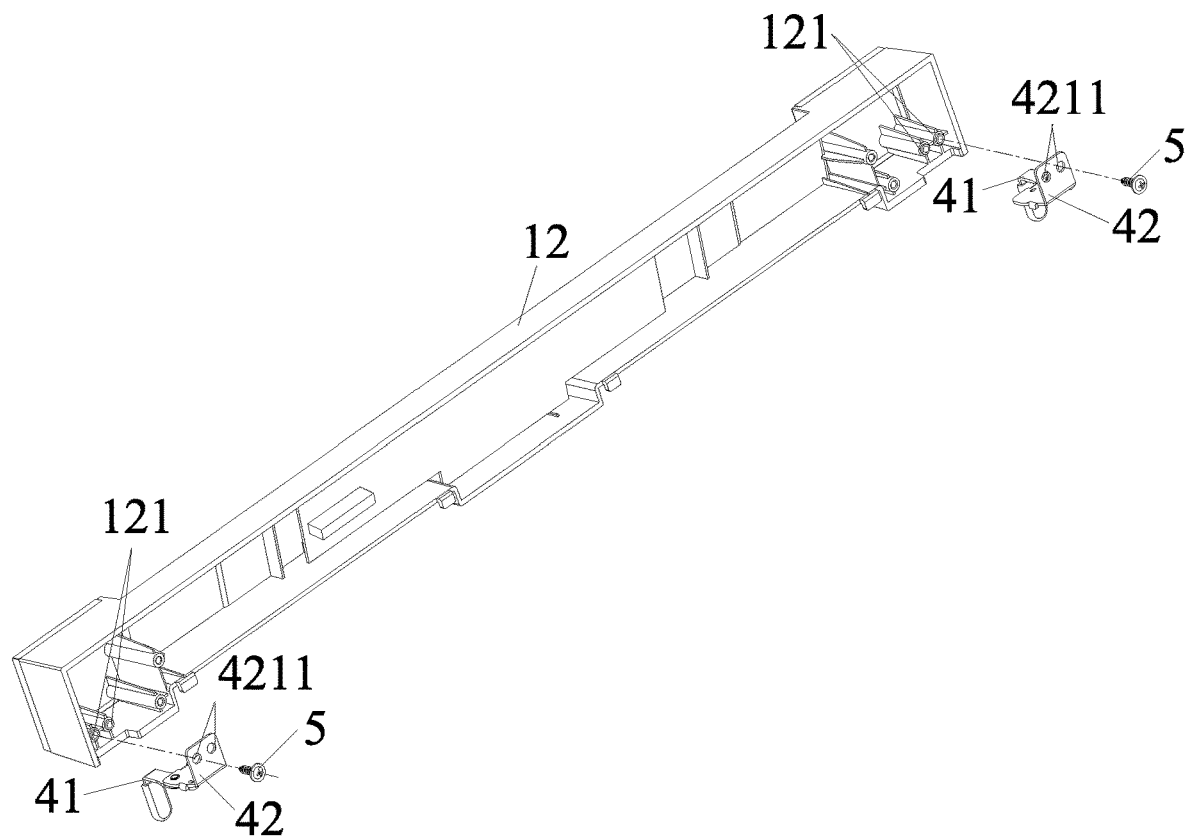
FIG. 9 is a three-dimensional structural diagram in the assembly process of the position-limiting lock assembly shown in FIG. 7 and the control panel.

In an embodiment of the present disclosure, as shown in FIG. 7 to FIG. 9, the position-limiting lock assembly 4 further includes a fixed base 42, the fixed base 42 includes a fixed portion 421 and a second connecting portion 422 connected to the fixed portion 421, the fixed portion 421 is fixed on a rear side of the control panel 12, the second connecting portion 422 is located between the control panel 12 and the drawer cover 3, and the first connecting portion 411 is rotatably connected to the second connecting portion 422 through the rotating shaft.

In the above embodiment, the fixed base 42 is fixed on a rear side of the control panel 12, the lock 41 is connected to the fixed base 42, and then the control panel 12 is installed on the body 1 to install and fix the position-limiting lock assembly 4 on the body 1 simply and easily without affecting the overall structure of the microwave oven 100 with a drawer; and the first connecting portion 411 is rotatably connected to the second connecting portion 422 through the rotating shaft such that the lock 41 can rotate relative to the fixed base 42 and the extending portion 412 can rotate to the front and the side of the drawer cover 3. Preferably, the fixed base 42 is L-shaped, and the plane where the first connecting portion 411 is located is parallel to the plane where the second connecting portion 422 is located.

As for the fixing of the fixed base 42 on the control panel 12, preferably, as shown in FIG. 9, the fixed portion 421 is provided with a screw hole 4211, screw columns 121 are arranged on a rear side of the control panel 12, and the fixed base 42 is fixed on the control panel 12 through a screw 5.

Preferably, as shown in FIG. 8, the first connecting portion 411 is connected to the second connecting portion 422 through a rivet 43, and an elastic gasket 44 is arranged between the rivet 43 and the first connecting portion 411, thereby enhancing the mobility of the first connecting portion 411 relative to the second connecting portion 422, and relieving the friction between the first connecting portion 411 and the second connecting portion 422.

Preferably, as shown in FIG. 8 and FIG. 10 to FIG. 13, the surface of the first connecting portion 411 opposite to the second connecting portion 422 protrudes to form a protrusion 4111, and the second connecting portion 422 is provided with a first limiting hole 4221 and a second limiting hole 4222 matched with the protrusion 4111. When the extending portion 412 rotates to the front of the drawer cover 3, the protrusion 4111 is inserted into the first limiting hole 4221. When the extending portion 412 rotates to the side of the drawer cover 3, the protrusion 4111 is inserted into the second limiting hole 4222.

In the above embodiment, when the extending portion 412 rotates to the front and the side of the drawer cover 3, the protrusion 4111 is inserted into the first limiting hole 4221 and the second limiting hole 4222 respectively to position the lock 41 and prevent the user from excessively rotating the lock 41 or failing to rotate the lock 41 in place, so that when the drawer cover 3 is locked, the locking effect of the lock 41 on the drawer cover 3 is best, and after the drawer cover 3 is unlocked, the user can freely draw the drawer 2 out. Of course, the first connecting portion 411 may also be provided with a limiting hole, the second connecting portion 422 is provided with a first protrusion and a second protrusion on the end face opposite to the first connecting portion 411, and when the drawer cover 3 is unlocked or locked, the first protrusion and the second protrusion are inserted into the limiting hole respectively.

Figure 10:
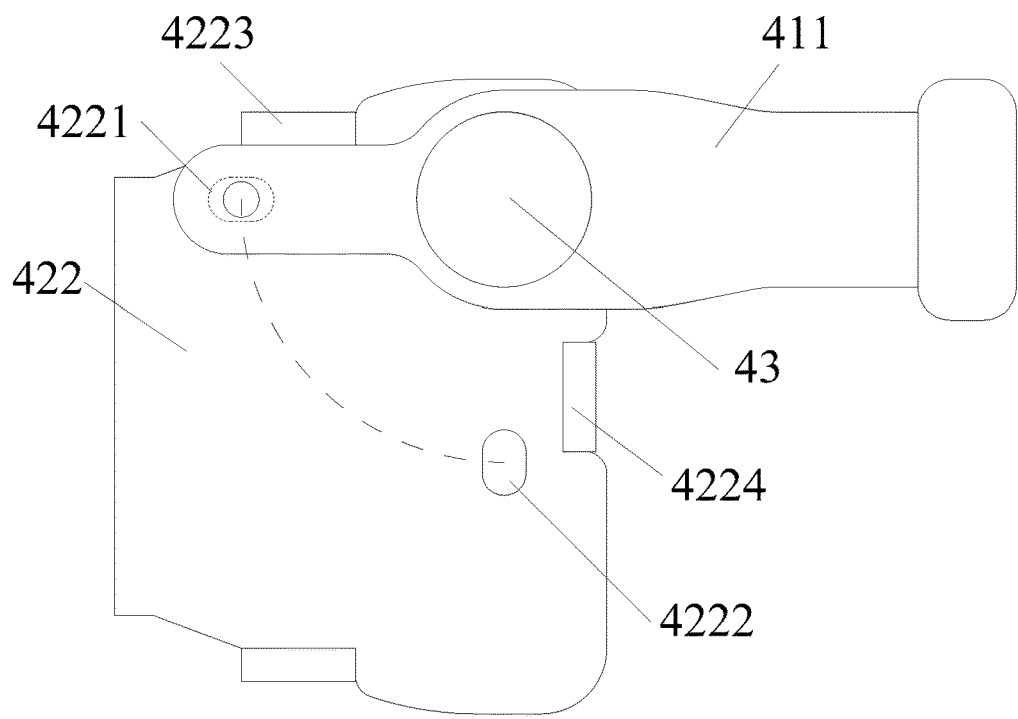
FIG. 10 is a bottom-view structure diagram of the position-limiting lock assembly according to an embodiment of the present disclosure when the drawer cover is locked.
Figure 11:
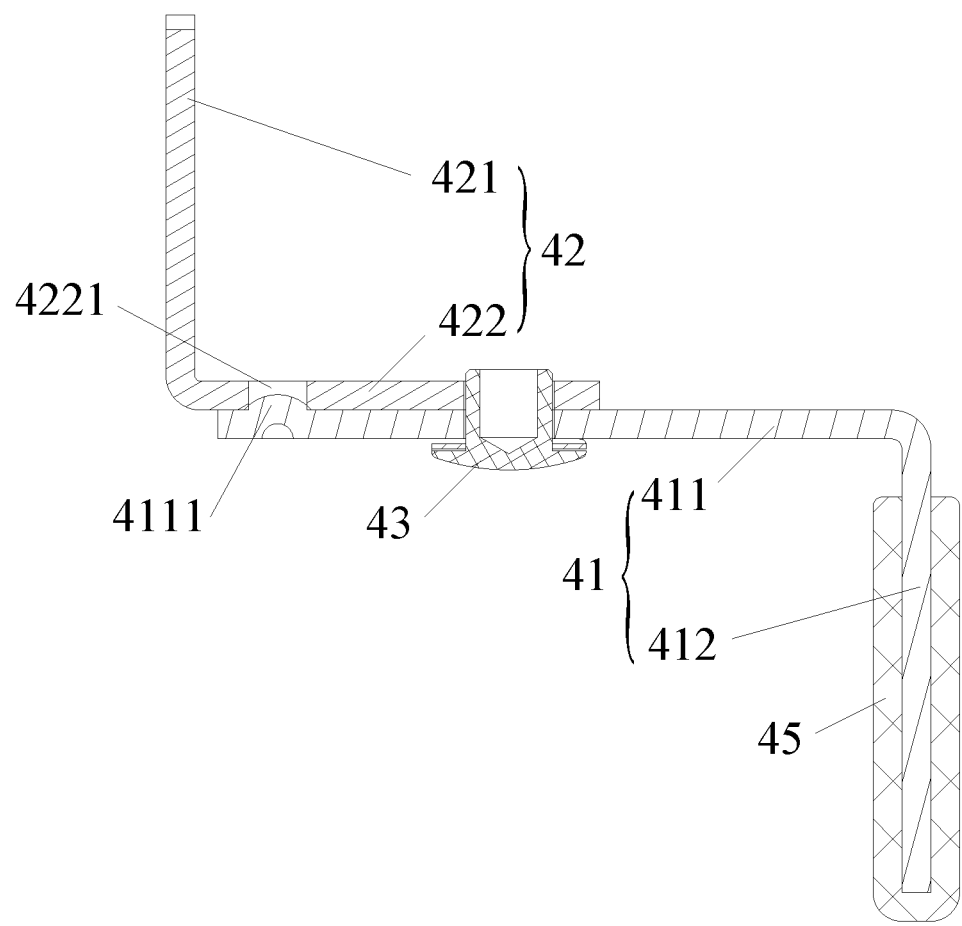
FIG. 11 is a sectional structure diagram of the position-limiting lock assembly shown in FIG. 10.
Figure 12:
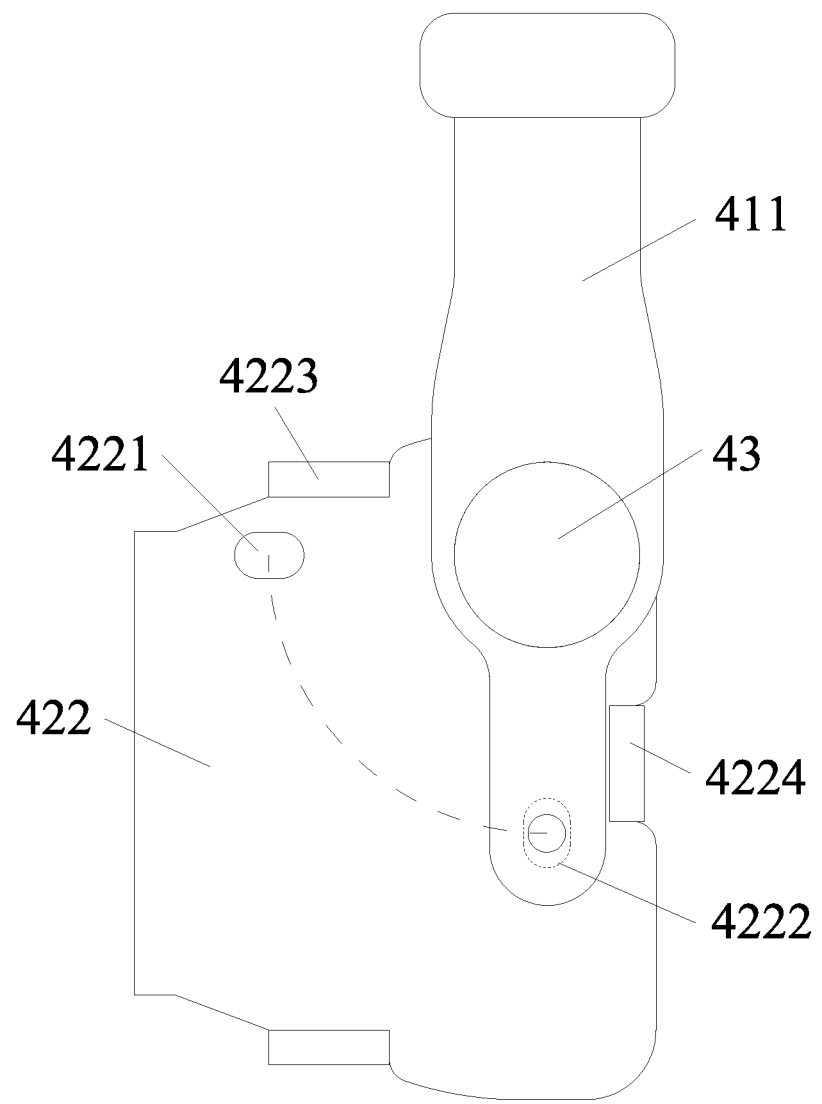
FIG. 12 is a bottom-view structure diagram of the position-limiting lock assembly according to an embodiment of the present disclosure when the drawer cover is unlocked.

Preferably, as shown in FIG. 10 to FIG. 12, the protrusion 4111 and the extending portion 412 are located on two sides of the rivet 43, that is, the protrusion 4111 is located at the free end of the first connecting portion 411. Since the free end has good elastic deformation capability, when the protrusion 4111 is arranged at the free end, the first connecting portion 411 can be positioned, and the rotating capability of the lock 41 relative to the fixed base 42 is not reduced.

Figure 13:
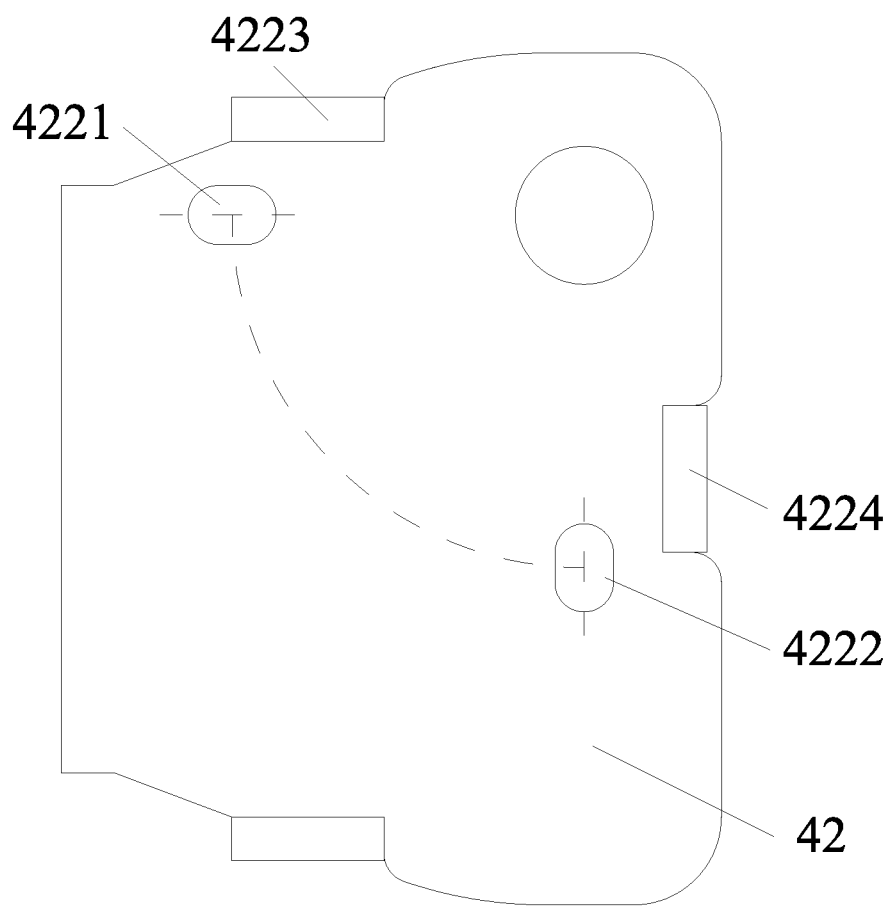
FIG. 13 is a bottom-view structure diagram of a fixed base according to an embodiment of the present disclosure.

Further, as shown in FIG. 13, both the first limiting hole 4221 and the second limiting hole 4222 are elliptical, and major axes of the two ellipses are perpendicular to each other.

In the above embodiment, preferably, the long axes of the ellipses are located in the radial direction of rotation of the first connecting portion 411, so as to enhance the positioning capability of the first limiting hole 4221 and the second limiting hole 4222 to the protrusion 4111. The straight lines where the long axes of the two ellipses are located are perpendicular to each other such that when the drawer cover 3 enters the unlocked state from the locked state, the first connecting portion 411 is rotated 90° conveniently; when the drawer cover 3 is in the locked state, the extending portion 412 is located in front of the drawer cover 3 to achieve a best locking effect; and when the drawer cover 3 is in the unlocked state, the extending portion 412 is completely located on the side of the drawer cover 3 and does not interfere with the draw-out operation on the drawer cover 3 to ensure that the drawer cover 3 is freely drawn out and pushed in.

Further, as shown in FIG. 8 and FIG. 10 to FIG. 13, the surface of the second connecting portion 422 opposite to the first connecting portion 411 protrudes to form a first limit stop 4223 and a second limit stop 4224, and the first connecting portion 411 rotates within a limit space formed by the first limit stop 4223 and the second limit stop 4224. When the extending portion 412 rotates to the front of the drawer cover 3, one side wall of the first connecting portion 411 abuts against the first limit stop 4223. When the extending portion 412 rotates to the side of the drawer cover 3, the other side wall of the first connecting portion 411 abuts against the second limit stop 4224.

In the above embodiment, the extending portion 412 rotates between the first limit stop 4223 and the second limit stop 4224. When the drawer cover 3 is locked, one side wall of the first connecting portion 411 abuts against the first limit stop 4223, and when the drawer cover 3 is unlocked, the other side wall of the first connecting portion 411 abuts against the second limit stop 4224, thereby limiting the angle range of rotation of the lock 41. When the user uses it, the extending portion 412 is rotated to a position where the side wall of the first connecting portion 411 abuts against the first limit stop 4223 or the second limit stop 4224, such that the drawer cover 3 is completely locked or unlocked. Preferably, the second connecting portion 422 is provided with the first limiting hole 4221, the second limiting hole 4222, the first limit stop 4223 and the second limit stop 4224 at the same time, so that when the protrusion 4111 is separated from the first limiting hole 4221 or the second limiting hole 4222 due to overexertion of the user rotating the lock 41, the first limit stop 4223 and the second limit stop 4224 can continue to play a role in limiting and positioning to enhance the use reliability and stability of the position-limiting lock assembly 4.

Figure 2:
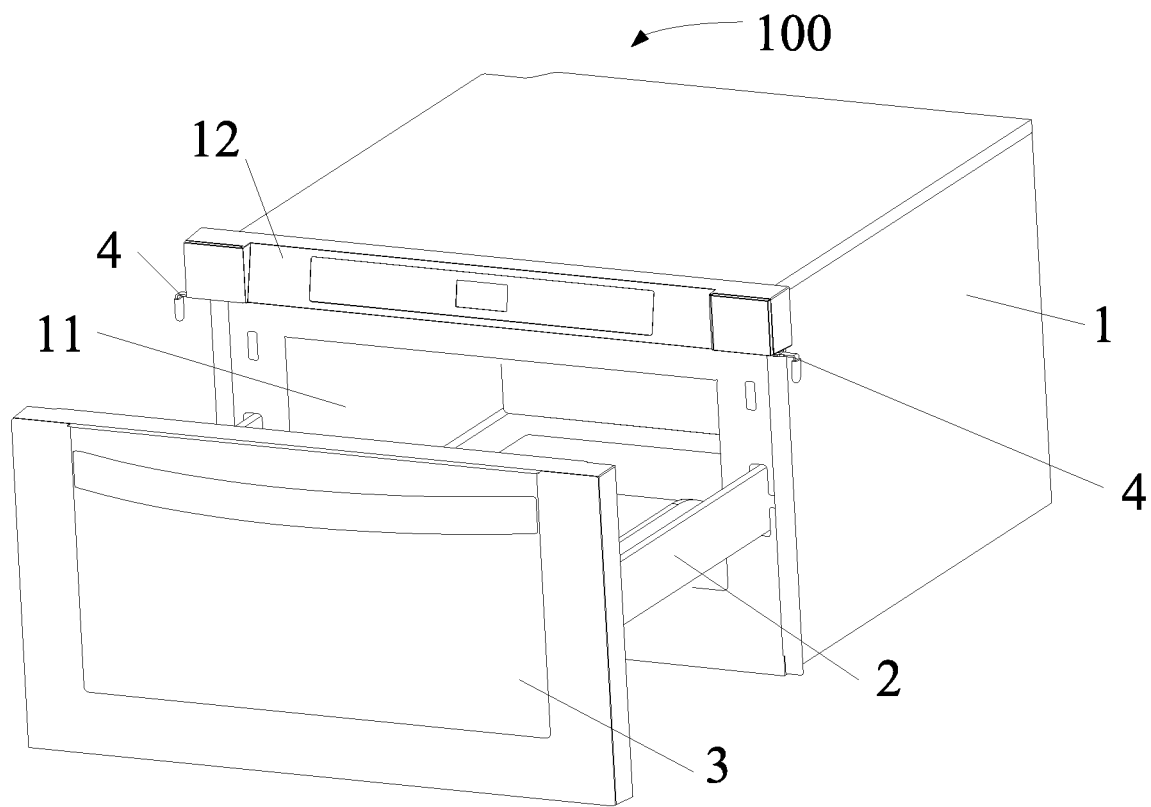
FIG. 2 is a three-dimensional structure diagram of the microwave oven with a drawer according to an embodiment of the present disclosure when the drawer is drawn out.
Figure 3:
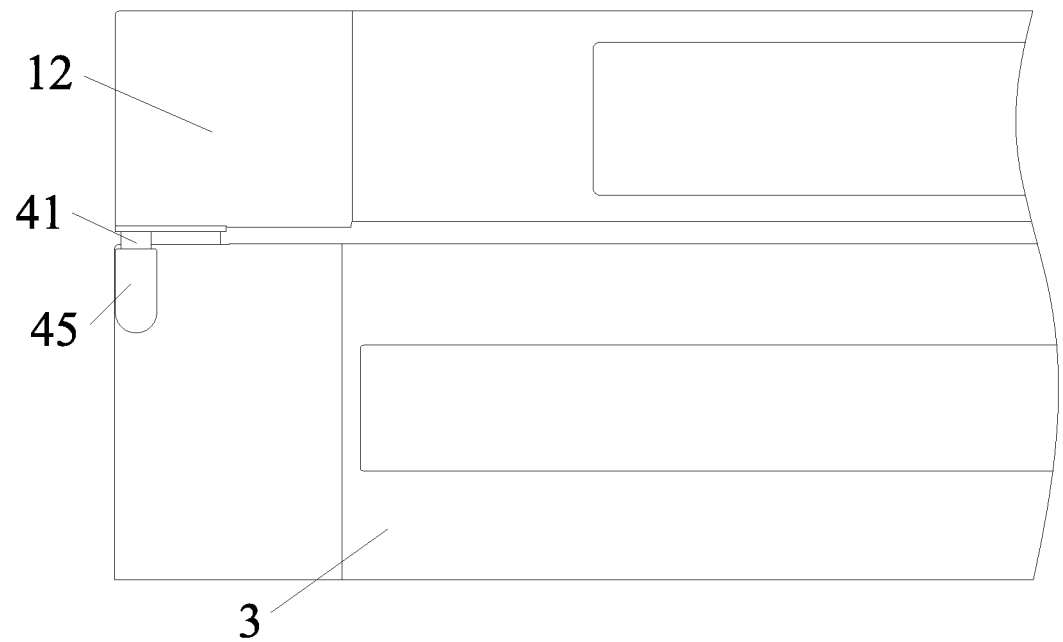
FIG. 3 is a partial front-view structure diagram of the microwave oven with a drawer according to an embodiment of the present disclosure when a drawer cover is locked.
Figure 4:
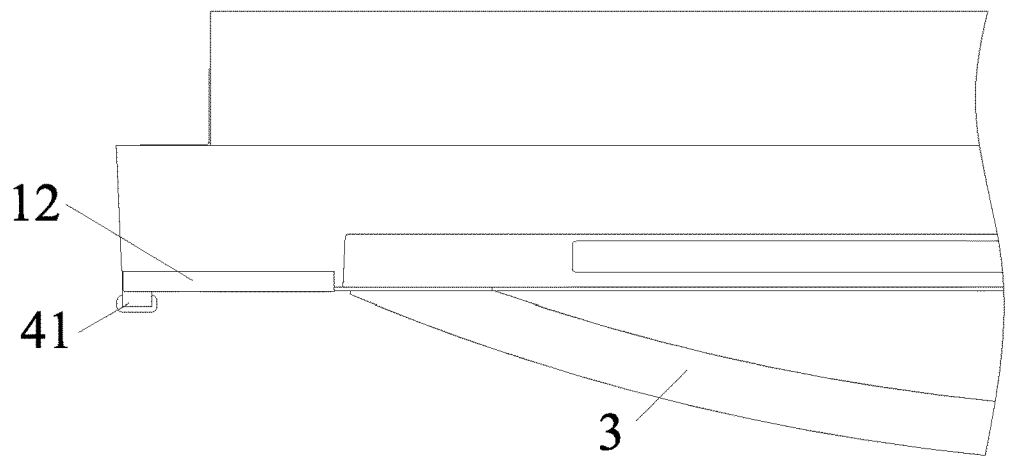
FIG. 4 is a partial top-view structure diagram of the microwave oven with a drawer according to an embodiment of the present disclosure when the drawer cover is locked.
Figure 5:
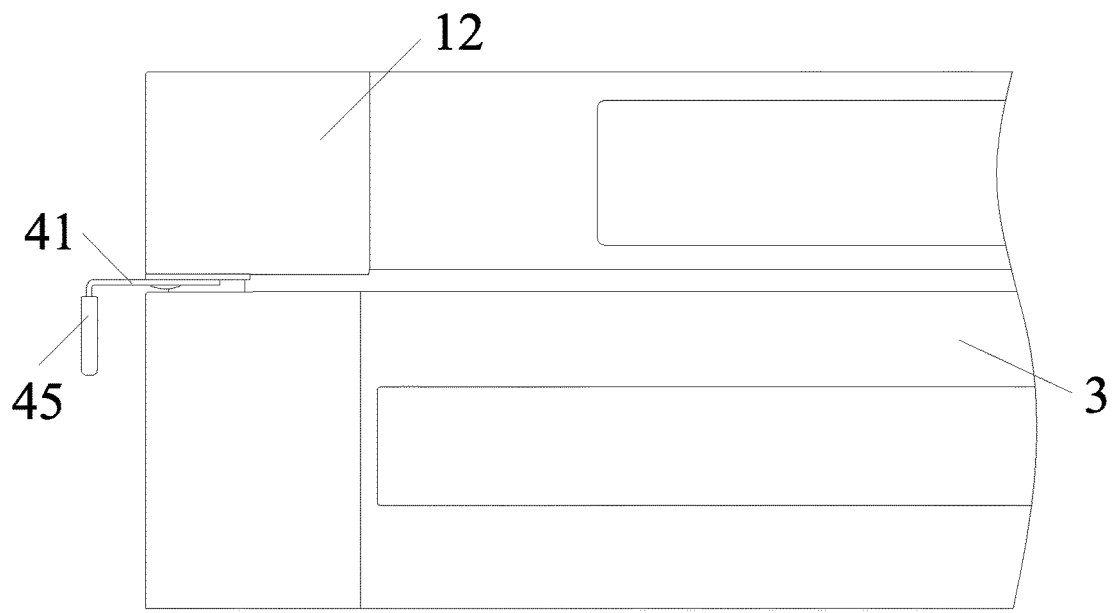
FIG. 5 is a partial front-view structure diagram of the microwave oven with a drawer according to an embodiment of the present disclosure when the drawer cover is unlocked.
Figure 6:
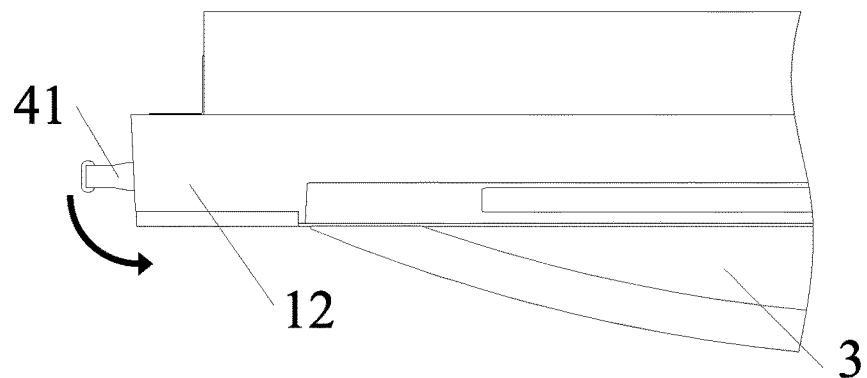
FIG. 6 is a partial top-view structure diagram of the microwave oven with a drawer according to an embodiment of the present disclosure when the drawer cover is unlocked, wherein the curved arrow represents the direction of rotation of the lock when the drawer cover is locked.

Preferably, as shown in FIG. 1 and FIG. 2, the microwave oven 100 with a drawer is provided with two position-limiting lock assemblies 4, the two position-limiting lock assemblies 4 are respectively located at the left and right ends of the control panel 12, the right lock 41 is rotated right to the right side of the drawer cover 3, and the left lock 41 is rotated left to the left side of the drawer cover 3, thus unlocking the drawer cover 3; and the right lock 41 is rotated left to the front of the drawer cover 3, and the left lock 41 is rotated right to the front of the drawer cover 3, thus locking the drawer cover 3.

In the second embodiment of the present disclosure, the position-limiting lock assembly 4 is located on the front end face of the body 1, one end of the lock 41 is rotatably connected to the body 1 through the rotating shaft, and the rotating shaft is arranged in the horizontal direction, so that the lock 41 rotates within a vertical plane and can rotate to the front of the drawer cover 3 and above the drawer cover 3.

In the above embodiment, the position-limiting lock assembly 4 is located on the front end face of the body 1 and above the accommodation cavity 11, one end of the lock 41 is rotatably connected to the body 1 through the rotating shaft, the other end protrudes from the front opening of the accommodation cavity 11, and the lock 41 rotates within the vertical plane; when the lock 41 rotates down, the other end of the lock 41 is located in front of the drawer cover 3 to lock the drawer cover 3; and when the lock 41 rotates up, the other end of the lock 41 is located above the drawer cover 3 to unlock the drawer cover 3.

Preferably, as shown in FIG. 1, the microwave oven 100 with a drawer can be installed in a cabinet 6.

To sum up, in the kitchen appliance with a drawer according to the embodiments of the present disclosure, one end of the lock 41 is rotatably connected to the body 1, and the other end of the lock 41 protrudes from the front opening of the body 1, such that the other end of the lock 41 can rotate to the front of the drawer cover 3 to lock the drawer cover 3 and the drawer 2 cannot be pulled out of the accommodation cavity 11. In this way, when the kitchen appliance with a drawer is applied to a mobile environment such as a train, the drawer 2 will not be opened due to inertia or road unevenness or other external factors, thereby preventing the contents inside the drawer 2 from being thrown out, preventing children from opening the drawer 2 and exposing themselves to danger such as pinching or scald, and enhancing the use safety of the kitchen appliance with a drawer.

In the description of the present disclosure, unless otherwise specified, the terms "connected", "fixed" and the like all should be generally understood, for example, the "connected" may be fixedly connected, detachably connected, integrally connected, electrically connected, directly connected or indirectly connected through a medium. Those of ordinary skill in the art can understand the specific meanings of the above terms in the present disclosure according to specific circumstances.

In the description of this specification, it should be understood that the terms "upper", "lower", "front", "back", "left", "right" and the like indicate the orientation or position relationship based on the orientation or position relationship shown in the drawings. The terms are only for description convenience of the present disclosure and simplification of the description, but do not indicate or imply that the pointed devices or units must have specific directions or be constructed and operated in specific orientations. Therefore, the terms should not be understood to limit the present disclosure.

In the description of this specification, the terms "one embodiment", "some embodiments", "a specific embodiment" and the like mean that specific features, structures, materials or characteristics described in conjunction with the embodiments or examples are included in the at least one embodiment or example of the present disclosure. In this specification, the schematic descriptions of the above terms do not necessarily refer to the same embodiment or example. Moreover, the specific features, structures, materials or characteristics described may be combined appropriately in one or more embodiments or examples.

Described above are merely preferred embodiments of the present disclosure, and the present disclosure is not limited thereto. Various modifications and variations may be made to the present disclosure for those skilled in the art. Any modification, equivalent substitution or improvement made within the spirit and principle of the present disclosure shall fall into the protection scope of the present disclosure.

What is claimed is:

1. A kitchen appliance with a drawer, comprising:
    a body having an accommodation cavity of which a front end is provided with an opening;
    a drawer located in the accommodation cavity, wherein a drawer cover is fixedly attached to a front end of the drawer, and the drawer cover can drive the drawer to move relative to the body, so as to draw the drawer out of or push the drawer into the accommodation cavity; and
    a position-limiting lock assembly mounted on the body and above the accommodation cavity, wherein the position-limiting lock assembly has a lock, one end of the lock being rotatably connected to the body and the other end of the lock protruding from a front opening of the body, when the other end of the lock rotates to a position in front of the drawer cover, the drawer is restrained from being pulled out of the accommodation cavity, and when the other end of the lock rotates away from the position in front of the drawer cover, the drawer can be pulled out of the accommodation cavity, wherein:
        the position-limiting lock assembly is located close to a side wall of the body, the one end of the lock is rotatably connected to the body through a rotating shaft, and the rotating shaft is arranged in the vertical direction such that the lock can rotate within a horizontal plane from the front of the drawer cover to a side of the drawer cover;
        the lock is L-shaped and comprises a first connecting portion and an extending portion formed by bending extension of the first connecting portion, the first connecting portion is rotatably connected to the body through the rotating shaft, and the extending portion can rotate to a front and a side of the drawer cover; and
        the front end of the body is provided with a control panel located above the drawer cover, and the first connecting portion is located between the drawer cover and the control panel and rotatably connected to a bottom surface of the control panel through the rotating shaft.

2. The kitchen appliance with a drawer according to claim 1, wherein
    the position-limiting lock assembly further comprises a fixed base, the fixed base having a fixed portion and a second connecting portion connected to the fixed portion, the fixed portion is fixed on a rear side of the control panel, the second connecting portion is located between the control panel and the drawer cover, and the first connecting portion is rotatably connected to the second connecting portion through the rotating shaft.

3. The kitchen appliance with a drawer according to claim 2, wherein
    the first connecting portion is connected to the second connecting portion through a rivet, and an elastic gasket is arranged between the rivet and the first connecting portion.

4. The kitchen appliance with a drawer according to claim 2, wherein
    the first connecting portion forms a protrusion facing the second connecting portion, and the second connecting portion is provided with a first limiting hole and a second limiting hole matched with the protrusion; when the extending portion rotates to the front of the drawer cover, the protrusion is inserted into the first limiting hole; and when the extending portion rotates to the side of the drawer cover, the protrusion is inserted into the second limiting hole.

5. The kitchen appliance with a drawer according to claim 4, wherein
    both the first limiting hole and the second limiting hole are elliptical, and major axes of the two ellipses are perpendicular to each other.

6. The kitchen appliance with a drawer according to claim 2, wherein
    the second connecting portion forms a first limit stop and a second limit stop both facing the first connecting portion, and the first connecting portion is configured to rotate within a limit space formed by the first limit stop and the second limit stop; when the extending portion rotates to the front of the drawer cover, one side wall of the first connecting portion abuts against the first limit stop; and when the extending portion rotates to the side of the drawer cover, the other side wall of the first connecting portion abuts against the second limit stop.

* * * * *